United States Patent [19]

Murthy et al.

[11] Patent Number: 5,523,423
[45] Date of Patent: Jun. 4, 1996

[54] FORM OF FORM 1 RANITIDINE

[75] Inventors: Keshava Murthy; Bruno K. Radatus; Kanwarpal S. Swidhu, all of Brantford, Canada

[73] Assignee: ACIC (Canada) Inc., Brantford, Canada

[21] Appl. No.: 458,253

[22] Filed: Jun. 2, 1995

Related U.S. Application Data

[62] Division of Ser. No. 418,401, Apr. 7, 1995.

[51] Int. Cl.⁶ .................................................. C07D 307/52
[52] U.S. Cl. ............................................................. 549/495
[58] Field of Search ...................................... 549/491, 495

[56] References Cited

U.S. PATENT DOCUMENTS

| | | | |
|---|---|---|---|
| 4,128,658 | 12/1978 | Price et al. | 549/495 |
| 4,521,431 | 6/1985 | Crookes | 549/495 |
| 4,672,133 | 6/1987 | Crookes | 549/495 |

Primary Examiner—C. Warren Ivy
Assistant Examiner—Amelia Owens
Attorney, Agent, or Firm—Ivor M. Hughes; Neil H. Hughes; Marcelo K. Sarkis

[57] ABSTRACT

Process for the production of an improved form of Form 1 Ranitidine Hydrochloride having improved filtration and drying characteristics, said process comprising in a substantially anhydrous hydroxylic solvent, comprising at least one alkanol solvent having 3–4 carbon atoms, adding anhydrous hydrogen chloride gas to Ranitidine free base wherein said substantially anhydrous hydroxylic solvent has the characteristics that it solubilizes the Ranitidine free base and hydrogen chloride gas, and subsequently recovering the improved form of Form 1 Ranitidine Hydrochloride.

8 Claims, No Drawings

FORM OF FORM 1 RANITIDINE

This application is a divisional of application Ser. No. 08/418,401, filed Apr. 7, 1995 (status: Pending).

FIELD OF INVENTION

This invention relates to an improved form of Form 1 Ranitidine Hydrochloride and processes for the manufacture thereof.

BACKGROUND OF THE INVENTION

Canadian Letters Patent 1,099,268 (corresponding to U.S. Pat. No. 4,128,658 and U.K. Patent 1565966) teaches the medicine Ranitidine and salts thereof (including the hydrochloride salt) and processes for the manufacture thereof.

Canadian Letters Patent 1,202,638 (corresponding to U.S. Pat. Nos. 4,521,431 and 4,672,133) purports to teach a specific new form of Ranitidine Hydrochloride which form the Inventor, Mr. Derek L. Crookes, termed "Form 2" to purportedly distinguish the purportedly new form from the purported forms taught in the original patents (Canadian Letters Patent 1,099,268, U.S. Pat. No. 4,128,658, U.K. Patent 1565966 and all corresponding patents and which form taught by these patents the Inventor identified as Form 1 forms of Ranitidine Hydrochloride).

Mr. Crookes asserted in the later patents (Canadian Letters Patent 1,202,638 and U.S. Pat. Nos. 4,521,431 and 4,672,133) that the procedures for producing (crystallizing) Ranitidine Hydrochloride in accordance with the teachings of said U.K. Patent 1565966 (and thus under corresponding U.S. Pat. No. 4,128,658 and Canadian Letters Patent 1,099,268)

> does not have the desirable features of a manufacturing process described above and Form 1 of the hydrochloride salt has unsuitable filtration and drying characteristics (page 2, line 35–page 3, line 1 of Canadian Letters Patent 1,202,638)

The only method by which Mr. Derek L. Crookes could overcome the deficiencies and limitations of the purported Form 1 Ranitidine Hydrochloride was to develop a purported new form of Ranitidine Hydrochloride (identified as Form 2 to distinguish the purported new form from the old form (termed Form 1)) and which purported Form 2 Ranitidine Hydrochloride overcame the deficiencies and limitations of the purported Form 1 Ranitidine Hydrochloride.

It is therefore an object of this invention to provide an improved form of Form 1 Ranitidine Hydrochloride which overcomes the previously described deficiencies and limitations of previous forms of Form 1 Ranitidine Hydrochloride and to provide Form 1 Ranitidine Hydrochloride which has better filtration and drying characteristics.

It is a further object of this invention to provide processes for the manufacture of the improved form of Form 1 Ranitidine Hydrochloride which processes provide the improved form of Form 1 Ranitidine Hydrochloride consistently and in goods yields.

Further and other objects of the invention will be realized by those persons skilled in the art from the following Summary of the Invention and Detailed Description of Embodiments thereof.

In this regard should other salts of Ranitidine in a form which has unsuitable filtration and drying characteristics be developed, it is a further object of this invention to provide processes which can be used to produce a better form of the salt of Ranitidine which has acceptable filtration and drying characteristics.

SUMMARY OF THE INVENTION

According to one aspect of the invention, a new process for consistently producing Form 1 Ranitidine Hydrochloride having improved filtration and drying characteristics is provided, the said process comprising adding a solution of anhydrous hydrogen chloride gas in substantially anhydrous isopropanol to a solution of Ranitidine Free Base in substantially anhydrous isopropanol preferably containing seeds of Form 1 Ranitidine Hydrochloride (for example the Ranitidine Hydrochloride termed Form 1 by Glaxo Group Limited produced under Canadian Letters Patent 1,099,268) at for example temperatures in the order of between about 40° C. to about 55° C. and subsequently recovering (as by crystallization through precipitation) the improved Form 1 Ranitidine Hydrochloride as for example by filtration and/or centrifuging. The isopropanol is expected to be anhydrous; however small amounts of water (for example less than about 2% preferably less than about 1% and more preferably less than about 0.5%) are not deleterious to the processes.

All or some of the isopropanol solvent which is preferred can be substituted by other suitable hydroxylic solvents such as a combination of anhydrous isopropanol with anhydrous ethanol or anhydrous methanol, anhydrous n-butanol, anhydrous propanol or anhydrous isobutanol and the like, with or without an anti-solvent (for example ethyl acetate) provided the hydroxylic solvent solubilizes each of Ranitidine Free Base and anhydrous hydrogen chloride gas and precipitates the desired form of Form 1 Ranitidine. Hydrochloride preferably slowly and uniformly. Anhydrous n-butanol or anhydrous isobutanol with or without anhydrous isopropanol can also be used. Persons skilled in the art given the above teachings will perceive other suitable solvents (which may be an alkanol or combination of alkanols at least one of which has 3–4 carbon atoms). The solvent should once again be substantially anhydrous and may carry a small amount of water for example less than about 2%, preferably less than about 1% and more preferably less than about 0.5%.

Thus, according to another aspect of the invention a new process for consistently producing an improved form of Form 1 Ranitidine Hydrochloride having improved filtration and drying characteristics is provided, the said process comprising adding an anhydrous solution of anhydrous hydrogen chloride gas in a substantially anhydrous hydroxylic solvent for example including an alkanol having 3 or 4 carbon atoms, to an anhydrous solution of Ranitidine Free Base in the same or different substantially anhydrous hydroxylic solvent suitable for the purposes of the process (and preferably including the same alkanol having 3 or 4 carbon atoms) and preferably containing seeds of Form 1 Ranitidine Hydrochloride preferably at temperatures in the order of 40° C.–55° C. and subsequently recovering the improved form of Form 1 Ranitidine Hydrochloride wherein the said substantially anhydrous solvent or solvents has/have the characteristics that each solubilizes each of Ranitidine Free Base and anhydrous hydrogen chloride gas and precipitates the desired form of Form 1 Ranitidine Hydrochloride slowly and uniformly.

Where other salts of Ranitidine are in a form having unsatisfactory filtration and drying characteristics, they may be converted to a suitable form by the processes of this invention modified in such manner to produce the desired salt and form consistent with this invention having satisfactory filtration and drying characteristics. In this embodiment, one skilled in the art would substitute the anhydrous hydrogen chloride by a suitable anhydrous acid which would yield the desired salt.

For most consistency, the process is carried out in a temperature range of between about 40° C. and about 55° C. when using isopropanol. Persons skilled in the art will appreciate that the temperature range is given as a guide and may vary with the choice of solvent.

Where anhydrous isopropanol and ethanol are used as the solvent with an anti-solvent ethyl acetate, the Ranitidine Free Base may be dissolved in the isopropanol and ethanol combination and the hydrogen chloride gas may be dissolved in the ethyl acetate and the solutions combined. Preferably however a single solvent is used as it is more easily recovered and recycled and preferably the solvent is isopropanol.

According to another aspect of the invention, an improved physical form of Form 1 Ranitidine Hydrochloride is provided, the improved form of Form 1 Ranitidine Hydrochloride being hard dense crystals (thus being heavier and more dense than previously known forms of Form 1 Ranitidine Hydrochloride), providing improved drying characteristics and providing a particle and crystal size which provides improved filtration characteristics over the previous Form 1 Ranitidine Hydrochloride which when produced in accordance with the teachings of Canadian Letters Patent 1,099,268 tended to retain more solvent during filtration, making drying more difficult.

In this regard, the improved form of Form 1 Ranitidine Hydrochloride now has characteristics of being harder and denser, and providing larger sized crystals. The following characteristics are typical of the recovered Form 1 Ranitidine Hydrochloride:

Bulk Density not less than about 0.23 gm/ml

Tap Density not less than about 0.28 gm/ml

Melting Point same as Form 1

Infrared Spectrum same as Form 1

Raman Spectrum same as Form 1

The fact that the Tap and Bulk Densities are relatively close to one another, indicates that the product produced is relatively hard and therefore will retain very little solvent as opposed to a previous form of Form 1 Ranitidine Hydrochloride (produced under Canadian Letters Patent 1,099,268), which was considered to be light and fluffy.

Because of the preferred methods of manufacture, the improved form of Form 1 of Ranitidine Hydrochloride is purer with a lesser number of impurities incorporated into the crystalline structure. Infrared Spectrum analysis was conducted on the samples and the resultant spectrum was consistent with the published data in respect of Form 1 Ranitidine Hydrochloride. The Infrared Spectrum Pattern was not consistent with the corresponding published data on Form 2 Ranitidine Hydrochloride. Raman Spectroscopy was performed which confirmed the production of Form I Ranitidine Hydrochloride.

Form 2 Ranitidine Hydrochloride may be converted to Form 1 Ranitidine Hydrochloride by the above methods. In this regard for example the Form 2 Ranitidine Hydrochloride may be dissolved in anhydrous methanol and heated. Anhydrous isopropanol alcohol warmed to 45° C. is added and the solution is seeded with Form 1 Ranitidine Hydrochloride. On cooling Form 1 Ranitidine Hydrochloride crystals can be recovered.

The following examples are offered as examples of the invention and are not to be interpreted as limiting the scope of the invention.

EXAMPLE 1

Ranitidine Hydrochloride (Form #1)

Preparation in Isopropyl Alcohol from Ranitidine Base

Ranitidine base (31.44 g, 0.1 mol) was dissolved in anhydrous isopropyl alcohol (isopropanol) (160 mL) by warming to 30° C., filtering through celite and washing the cake with anhydrous isopropyl alcohol (68 mL). The solution was warmed to 43° C., seeds (Form #1, 0.2g) were added and anhydrous hydrogen chloride in anhydrous isopropyl alcohol (15.19 g, 24%, 1 equivalent) was added all at once. The temperature rose to 51° C. and the temperature was maintained at 45°–50° C. for 5 hours while the product crystallized. The mixture was allowed to cool to 25° C. The precipitate was filtered and washed with anhydrous isopropyl alcohol (2×30 mL) to yield damp Ranitidine Hydrochloride. Vacuum drying at 40° C. overnight yields 34.26 g (0.0977 mol, 97.7%) of pure Ranitidine Hydrochloride (Form #1). The I.R. in KBr of the crystals conformed to Form #1.

EXAMPLE 2

Ranitidine Hydrochloride (Form #1)

Conversion of Form #2 to Form #1

Ranitidine Hydrochloride Form #2 (5.0g) was dissolved in anhydrous methanol (15 mL) warmed to 50° C. To this solution of methanol anhydrous isopropyl alcohol (19 mL) warmed to 45° C. and Form #1 seeds (0.1 g) were added simultaneously over a period of 5 minutes. After 30 minutes, another portion of anhydrous isopropyl alcohol (18 mL) was added. The mixture was stirred at 50° C. for 4 hours, cooled, filtered, and washed with isopropyl alcohol (15 mL). The isopropyl alcohol damp crystals were vacuum dried at 40° C. overnight to yield 3.78 g (75.6%) of Ranitidine Hydrochloride Form #1. The I.R. spectrum showed that the crystals conformed to Form #1.

As many changes can be made to the preferred embodiments of the invention without departing from the scope of the invention; it is intended that all material contained herein be interpreted as illustrative of the invention and not in a limiting sense.

The embodiments of the invention in which an exclusive property or privilege is claimed are as follows:

1. An improved form of Form 1 Ranitidine Hydrochloride having improved drying and filtration characteristics and having:

(i) a bulk density of not less than about 0.23 gm/ml; and (ii) a tap density of not less than about 0.28 gm/ml.

2. An improved form of Form 1 Ranitidine Hydrochloride having improved drying and filtration characteristics and having:

(i) a bulk density of not less than about 0.23 gm/ml; and (ii) a tap density of not less than about 0.28 gm/ml when produced according to a process selected from the group of processes consisting of the following processes:

(i) process for the production of an improved form of Form 1 Ranitidine Hydrochloride having improved filtration and drying characteristics, said process comprising in a substantially anhydrous hydroxylic solvent, comprising at least one alkanol solvent having 3–4 carbon atoms, adding anhydrous hydrogen chloride gas to Ranitidine free base wherein said substantially anhydrous hydroxylic solvent has the characteristics that it solubilizes the Ranitidine free base and hydrogen chloride gas, and subsequently recovering the improved form of Form 1 Ranitidine Hydrochloride;

(ii) process for the production of a improved form of Form 1 Ranitidine Hydrochloride having improved filtration and drying characteristics, said process comprising adding Ranitidine Hydrochloride to a substantially anhydrous hydroxylic solvent comprising at least one alkanol having 3–4 carbon atoms, which has the characteristics that it dissolves Ranitidine Hydrochloride and subsequently recovering the improved form of Form 1 Ranitidine Hydrochloride;

(iii) the process of sub-paragraph (i) or (ii) wherein the solution is in the order of between about 40° C. to about 55° C. when the improved form of Form 1 Ranitidine Hydrochloride is crystallized from the solution;

(iv) the process of sub-paragraph (i) wherein the anhydrous hydrogen chloride gas is introduced to the solution of Ranitidine free base as an anhydrous solution;

(v) the process of sub-paragraph (i), (ii), (iii), or (iv) wherein the hydroxylic solvent is a lower alkanol having 3 to 4 carbon atoms; and, (vi) the process of sub-paragraph (i), (ii), (iii), (iv), or (v) wherein the solvent comprises isopropanol.

3. An improved form of Form 1 Ranitidine Hydrochloride made according to the process of sub-paragraph (i) of claim 2.

4. An improved form of Form 1 Ranitidine Hydrochloride made according to the process of sub-paragraph (ii) of claim 2.

5. An improved form of Form 1 Ranitidine Hydrochloride made according to the process of sub-paragraph (iii) of claim 2.

6. An improved form of Form 1 Ranitidine Hydrochloride made according to the process of sub-paragraph (iv) of claim 2.

7. An improved form of Form 1 Ranitidine Hydrochloride made according to the process of sub-paragraph (v) of claim 2.

8. An improved form of Form 1 Ranitidine Hydrochloride made according to the process of sub-paragraph (vi) of claim 2.

* * * * *

UNITED STATES PATENT AND TRADEMARK OFFICE
CERTIFICATE OF CORRECTION

PATENT NO. : 5,523,423
DATED : June 4, 1996
INVENTOR(S) : Keshava Murthy, et. al.

It is certified that error appears in the above-indentified patent and that said Letters Patent is hereby corrected as shown below:

Title page, item [75], Inventors:  Third inventor's name should read--
Kanwar Pal singh sidhu--.

Signed and Sealed this

Twenty-fourth Day of September, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT : 5,523,423

DATED : June 4, 1996

INVENTOR(S) : Keshava Murthy, et al

It is certified that error appears in the above-identified patent and that said Letters Patent is hereby corrected as shown below:

Title page, item [75] Inventors:   Third inventor's name should read
--Kanwar Pal  S. Sidhu--.

Signed and Sealed this

Tenth Day of March, 1998

*Attest:*

BRUCE LEHMAN

*Attesting Officer*          *Commissioner of Patents and Trademarks*